United States Patent [19]

Gayer et al.

[11] Patent Number: 4,689,343
[45] Date of Patent: * Aug. 25, 1987

[54] NOVEL THIOLANE-2,4-DIONE-3-CARBOXAMIDE FUNGICIDES

[75] Inventors: Herbert Gayer, Monheim; Wilhelm Brandes, Leichlingen; Gerd Hänssler; Paul Reinecke, both of Leverkusen, all of Fed. Rep. of Germany

[73] Assignee: Bayer Aktiengesellschaft, Leverkusen, Fed. Rep. of Germany

[*] Notice: The portion of the term of this patent subsequent to Jul. 8, 2003 has been disclaimed.

[21] Appl. No.: 853,826

[22] Filed: Apr. 21, 1986

Related U.S. Application Data

[63] Continuation-in-part of Ser. No. 675,159, Nov. 27, 1984, Pat. No. 4,599,350.

[51] Int. Cl.[4] .................... A01N 43/02; C07D 333/32
[52] U.S. Cl. .................................... 514/445; 514/444; 549/60; 549/64
[58] Field of Search ................. 514/445, 444; 549/64, 549/60

[56] References Cited

U.S. PATENT DOCUMENTS 4,599,350  7/1986  Gayer et al. .................. 514/445

FOREIGN PATENT DOCUMENTS 3427847  6/1985  Fed. Rep. of Germany ........ 549/64

Primary Examiner—Alan Siegel
Attorney, Agent, or Firm—Sprung Horn Kramer & Woods

[57] ABSTRACT

Novel fungicidal active thiolane-2,4-dione-3-carboxamides of the formula

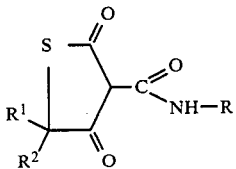

in which
R is alkyl, cycloalkyl, optionally substituted aralkyl or optionally substituted aryl, and
$R^1$ and $R^2$ each independently is hydrogen, alkyl, cycloalkyl, cycloalkylalkyl, aralkyl or aryl.

5 Claims, No Drawings

NOVEL THIOLANE-2,4-DIONE-3-CARBOXAMIDE FUNGICIDES

This application is a continuation-in-part of Ser. No. 675,159 filed on Nov. 27, 1984, now U.S. Pat. No. 4,599,350.

The invention relates to new thiolane-2,4-dione-3-carboxamides, a process for their preparation and their use as agents for combating pests.

It is already known that some tetrahydrothiopyran-3,5-dione-4-carboxamides, such as, for example, tetrahydrothiopyran-3,5-dione-4-[N-(4-chlorophenyl)]-carboxamide or tetrahydrothiopyran-3,5-dione-4-[N-(3,4-dichlorophenyl)]-carboxamide, which are known as insecticides have fungicidal side effects (compare Japanese Pat. No. 77 46,078 of Apr. 12, 1977).

The action of these compounds, however, is not always completely satisfactory, especially when low amounts and concentrations are applied.

New thiolane-2,4-dione-3-carboxamides of the general formula (I)

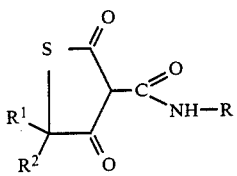

in which
R represents alkyl, cycloalkyl, optionally substituted aralkyl or optionally substituted aryl and
$R^1$ and $R^2$ independently of one another represent hydrogen, alkyl, cycloalkyl, cycloalkylalkyl, aralkyl or aryl,
have now been found.

The compounds of the formula (I) are in tautomeric equilibrium with compounds of the formulae (Ia), (Ib) and (Ic)

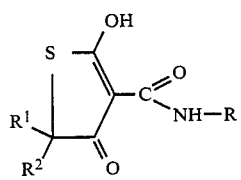

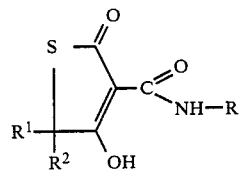

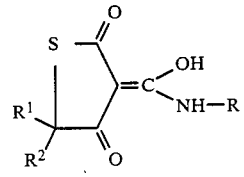

The enol forms (Ia), (Ib) and (Ic), in particular, are stabilized by strong intramolecular hydrogen bridges.

The compounds of the formula (I) can furthermore be in the form of geometric and/or optical isomers or isomer mixtures of varying composition.

Both the pure isomers and the isomer mixture, as well as the various tautomeric structures, are claimed according to the invention.

It has furthermore been found that the new thiolane-2,4-dione-3-carboxamides of the general formula (I)

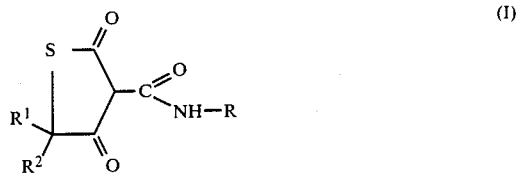

in which
R represents alkyl, cycloalkyl, optionally substituted aralkyl or optionally substituted aryl and
$R^1$ and $R^2$ independently of one another represent hydrogen, alkyl, cycloalkyl, cycloalkylalkyl, aralkyl or aryl,
are obtained by a process in which thiolane-2,4-dione-3-carboxylic acid esters of the formula (II)

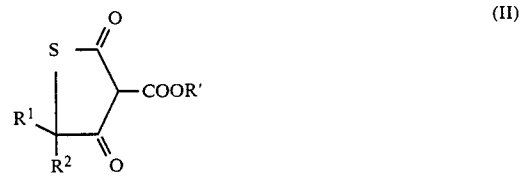

in which
$R^1$ and $R^2$ have the abovementioned meanings and
R' represents alkyl,
are reacted with amines of the formula (III)

$$H_2N-R \qquad (III)$$

in which
R has the abovementioned meanings,
if appropriate in the presence of a diluent.

Finally, it has been found that the new thiolane-2,4-thione-3-carboxamides have fungicidal properties.

Surprisingly, the thiolane-2,4-dione-3-carboxamides of the formula (I) according to the invention have a better fungicidal activity than the tetrahydrothiopyran-3,5-dione-4-carboxamides, such as, for example, tetrahydrothiopyran-3,5-dione-4-[N-(4-chlorophenyl)]-carboxamides or -4-[N-(3,4-dichlorophenyl)]-carboxamides, which are known from the prior art and are very closely related compounds chemically and from the point of view of their action.

Formula (I) provides a general definition of the thiolane-2,4-dione-3-carboxamides. Preferred compounds of the formula (I) are those in which
R represents straight-chain or branched alkyl with 1 to 8 carbon atoms, cycloalkyl with 3 to 7 carbon atoms, aralkyl which has 1 or 2 carbon atoms in the alkyl part and 6 to 10 carbon atoms in the aryl part and is optionally monosubstituted or polysubstituted by identical or different substituents, or aryl which has 6 to 10 carbon atoms and is optionally monosubstituted or polysubstituted by identical or different substituents, possible substituents on the aryl in each case being: halogen, cyano, nitro, straight-chain or branched alkyl with 1 to 16 carbon atoms, straight-chain or branched alkoxy and alkylthio with in each case 1 to 2 carbon atoms, halogenoalkyl, halogenoalkoxy and halogenoalkylthio with in each case 1 or 2 carbon atoms and up to 5 identical or different halogen atoms, dioxyalkylene which has 1 or 2 carbon atoms in the alkylene radical, is linked in two positions and is optionally monosubstituted or polysubstituted by identical or different halogen atoms or lower alkyl radicals, phenyl and phenoxy, each of which is optionally monosubstituted or polysubstituted by identical or different halogen atoms and lower alkyl and lower halogenoalkyl radicals, cycloalkyl with 5 to 7 carbon atoms, and alkoxycarbonylalkyl and alkoxycarbonylalkenyl with in each case 1 or 2 carbon atoms in the alkoxy part and in each case 1 to 2 carbon atoms in the alkyl or alkenyl part, and $R^1$ and $R^2$ independently of one another represent hydrogen, straight-chain or branched alkyl with 1 to 6 carbon atoms, cycloalkyl with 3 to 7 carbon atoms, cycloalkylalkyl with 3 to 7 carbon atoms in the cycloalkyl part and 1 to 2 carbon atoms in the alkyl part, phenylalkyl with 1 to 2 carbon atoms in the alkyl part or phenyl.

Particularly preferred compounds of the formula (I) are those in which

R represents straight-chain or branched alkyl with 1 to 6 carbon atoms, cyclopentyl, cyclohexyl, or phenyl, benzyl or naphthyl, each of which is optionally mono-, di- or tri-substituted by identical or different substituents, possible substituents in each case being: fluorine, chlorine, bromine, nitro, cyano, straight-chain or branched alkyl with 1 to 14 carbon atoms, methoxy, ethoxy, methylthio, trifluoromethyl, trifluoromethoxy and trifluoromethylthio, dioxymethylene, dioxyethylene and dioxytrifluorochloroethylene, each of which is linked in two positions, phenyl and phenoxy, each of which is optionally mono-, di- or tri-substituted by identical or different substitutents from the group comprising methyl, chlorine and trifluoromethyl, and cyclopentyl, cyclohexyl, 2-methoxycarbonylvinyl and 2-ethoxycarbonylvinyl, and $R^1$ and $R^2$ independently of one another represent hydrogen, methyl, ethyl, n- or i-propyl, n-, i-, s- or t-butyl, cyclohexyl, cyclohexylmethyl, benzyl or phenyl.

The following compounds of the general formula (I) may be mentioned specifically, in addition to the compounds mentioned in the preparation examples:

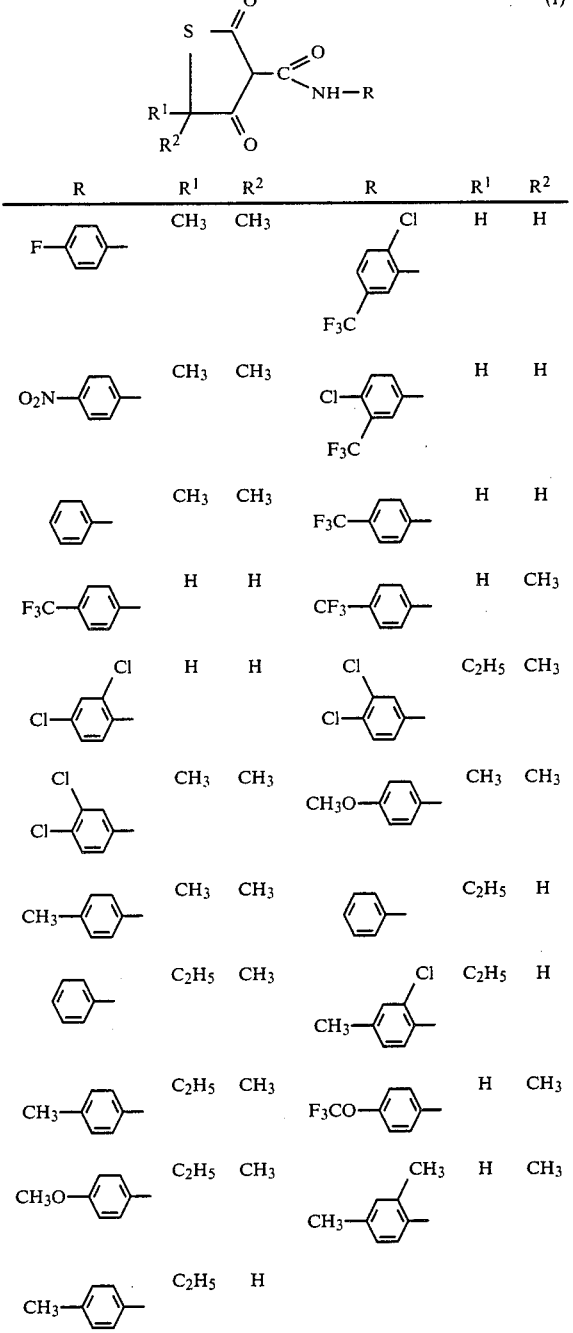

If, for example, ethyl 5-methylthiolane-2,4-dione-3-carboxylate and 4-bromoaniline are used as starting substances, the course of the reaction in the process according to the invention can be represented by the following equation:

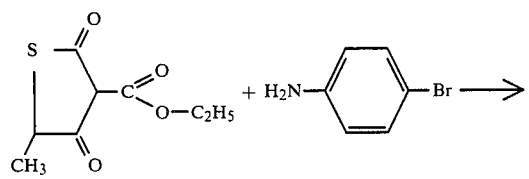

-continued

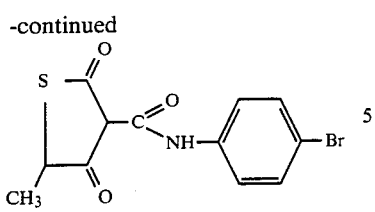

Formula (II) provides a general definition of the thiolane-2,4-dione-3-carboxylic acid esters required as starting substances for carrying out the process according to the invention. In this formula (II), $R^1$ and $R^2$ preferably represent those radicals which have already been mentioned as preferred for these substituents in the description of the substances of the formula (I) according to the invention, and $R'$ preferably represents straight-chain or branched alkyl with 1 to 4 carbon atoms, in particular methyl or ethyl.

Some of the thiolane-2,4-dione-3-carboxylic acid esters of the formula (II) are known (compare, for example, Chem. Ber. 46, 2103 (1913)). The representatives which are not yet known are obtained in an analogous manner by processes which are known in principle, by a procedure in which, in the 1st stage, α-halogenocarboxylic acids of the formula (IV)

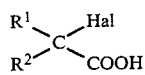 (IV)

in which
$R^1$ and $R^2$ have the abovementioned meanings and
Hal represents halogen, preferably chlorine or bromine,
are first reacted with mercaptoacetic acid or the sodium salts thereof, if appropriate in the presence of a diluent, such as, for example, tetrahydrofuran or water, and if appropriate in the presence of an acid-binding agent, such as, for example, triethylamine, at temperatures between −20° C. and +50° C., and the α-acetylthiocarboxylic acids thus obtained, of the formula (V)

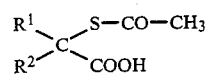 (V)

in which
$R^1$ and $R^2$ have the abovementioned meanings,
are reacted, in a 2nd stage, with a halogenating agent, such as, for example, thionyl chloride or oxalyl chloride, in a generally customary manner, if appropriate in the presence of a diluent, such as, for example, methylene chloride, at temperatures between −20° C. and +50° C. (compare, for example, J. Chem. Soc. C, 1968, 1504), and the α-acetylthiocarboxylic acid halides thus obtainable, of the formula (VI)

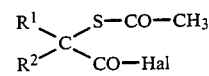 (VI)

in which
$R^1$ and $R^2$ have the abovementioned meanings and
Hal' represents halogen, in particular chlorine or bromine, are reacted, in a 3rd stage, with the sodium salt or ethoxy-magnesium salt of a malonic acid ester, of the formula (VII)

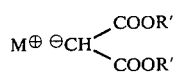 (VII)

in which
$R'$ has the abovementioned meaning and
$M^\oplus$ represents a sodium or ethoxy-magnesium cation,
if appropriate in the presence of a diluent, such as, for example, tetrahydrofuran, at temperatures between −20° C. and +50° C., and the malonic ester adducts thus obtainable, of the formula (VIII)

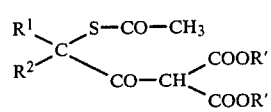 (VIII)

in which
$R^1$, $R^2$ and $R'$ have the abovementioned meanings,
are cyclized, in a 4th stage, if appropriate in the presence of a diluent, such as, for example, water, and if appropriate in the presence of a base, such as, for example, sodium hydroxide, at temperatures between 0° C. and 80° C.

Sodium salts of malonic acid esters, of the formula (VIII), mercaptoacetic acid and α-halogenocarboxylic acids of the formula (IV) are generally known compounds of organic chemistry.

Formula (III) provides a general definition of the amines furthermore required as starting substances for carrying out the process according to the invention. In this formula (III), R preferably represents those radicals which have already been mentioned as preferred for this substituent in the description of the substances of the formula (I) according to the invention.

The amines of the formula (III) are generally known compounds of organic chemistry.

If appropriate, the process according to the invention can be carried out in the presence of a diluent. Possible diluents are, in principle, all the inert organic solvents. Solvents which are preferably used are aromatic hydrocarbons, such as benzene, toluene or xylene; ethers, such as dioxane, tetrahydrofuran or ethylene glycol dimethyl or diethyl ether, or dipolar aprotic solvents, such as dimethylformamide, dimethylsulphoxide or hexamethylphosphoric acid triamide.

The process according to the invention can, however, also be carried out in the absence of a diluent.

The reaction temperatures can be varied within a substantial range in carrying out the process according to the invention. In general, the reaction is carried out between +50° C. and +200° C., preferably between +80° C. and +150° C.

For carrying out the process according to the invention, in general 1 to 2 moles, preferably equimolar amounts, of amine of the formula (III) are employed per mole of thiolane-2,4-dione-3-carboxylic acid ester of the formula (II). The reactants are heated, with or without a solvent, at the required reaction temperature for some minutes to some hours. On cooling of the reaction mixture, the desired end products of the formula (1) are as a rule obtained in a crystalline form which can be purified by recrystallization from a suitable solvent.

The active compounds according to the invention exhibit a powerful microbicidal action and can be employed in practice for combating undesired microorganisms. The active compounds are suitable for use as plant protection agents.

Fungicidal agents in plant protection are employed for combating plasmodiophoromycetes, Oomycetes, Chytridiomycetes, -Zygomycetes, Ascomycetes, Basidiomycetes and Deuteromycetes.

Bactericidal agents are employed in plant protection for combating Pseudomonadaceae, Rhizobiaceae, Enterobacteriaceae, Corynebacteriaceae and Streptomycetaceae.

The good toleration, by plants, of the active compounds at the concentrations required for combating plant diseases permits treatment of above-ground parts of plants, of vegetative propagation stock and seeds and of the soil.

The active compounds according to the invention can be used with particularly good success for combating cereal diseases, for example those caused by *Cochliobolus sativus, Septoria nodorum, Pyrenophora teres* and *Puccinia* species, for combating rice diseases, such as, for example, against the rice spot disease causative organism (*Pyricularia oryzae*) or against the rice disease causative organism (*Pellicularia sasakii*), or for combating fruit and vegetable diseases, such as, for example, against the leaf rot of tomato causative organism (*Phytophthora investans*) or against the causative organism of downy grape mildew (*Plasmopara viticola*).

In addition, the active compounds according to the invention also have a batericidal, insecticidal and insect growth-inhibiting action.

The active compounds can be converted to the customary formulations, such as solutions, emulsions, wettable powders, suspensions, powders, dusting agents, foams, pastes, soluble powders, granules, aerosols, suspension-emulsion concentrates, seed treatment powders, natural and synthetic materials impregnated with active compound, very fine capsules in polymeric substances and in coating compositions for seed, and formulations used with burning equipment, such as fumigating cartridges, fumigating cans, fumigating coils and the like, as well as ULV cold mist and warm mist formulations.

These formulations are produced in known manner, for example by mixing the active compounds with extenders, that is, liquid solvents, liquefied gases under pressure, and/or solid carriers, optionally with the use of surface-active agents, that is, emulsifying agents and/or dispersing agents, and/or foam-forming agents. In the case of the use of water as an extender, organic solvents can, for example, also be used as auxiliary solvents. As liquid solvents, there are suitable is the main: aromatics, such as xylene, toluene or alkyl naphthalenes, chlorinated aromatics or chlorinated aliphatic hydrocarbons, such as chlorobenzenes, chloroethylenes or methylene chloride, aliphatic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, strongly polar solvents, such as dimethylformamide and dimethylsulphoxide, as well as water; by liquefied gaseous extenders or carriers are meant liquids which are gaseous at normal temperature and under normal pressure, for example aerosol propellants, such as halogenated hydrocarbons as well as butane, propane, nitrogen and carbon dioxide; as solid carriers there are suitable: for example ground natural minerals, such as kaolins, clays, talc, chalk, quartz, attapulgite, montmorillonite, or diatomaceous earth, and ground synthetic minerals, such as highly-dispersed silicic acid, alumina and silicates; as solid carriers for granules there are suitable: for example crushed and fractionated natual rocks such as calcite, marble, pumice, sepiolite and dolomite, as well as synthetic granules of inorganic and organic meals, and granules of organic material such as sawdust, coconut shells, corn cobs and tobacco stalks; as emulsifying and/or foam-forming agents there are suitable: for example non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products; as dispersing agents there are suitable: for example ligninsulphite waste liquors and methylcellulose.

Adhesives such as carboxymethylcellulose and natural and synthetic polymers in the form of powders, granules or latices, such as gum arabic, polyvinyl alcohol and polyvinyl acetate, as well as naturally occurring phospholipids, such as cephalins and licithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalotyanine dyestuffs, and trace nutrients such as salts of iron, manganese, boron, copper, cobalt, molybdenum and zinc.

The formulations in general contain between 0.1 and 95 percent by weight of active compound, preferably between 0.5 and 90%.

The active compounds according to the invention can be present in the formulations or in the various use forms as a mixture with other known active compounds, such as fungicides, batericides, insecticides, acaricides, nematicides, herbicides, bird repellents, growth factors, plant nutrients and agents for improving soil structure.

The active compounds can be used as such or in the form of their formulations or the use forms prepared therefrom by further dilution, such as ready-to-use solutions, emulsions, suspensions, powders, pastes and granules. They are used in the customary manner, for example by watering, immersion, spraying, atomizing, misting, vaporizing, injecting, forming a slurry, brushing on, dusting, scattering, dry dressing, moist dressing, wet dressing, slurry dressing or encrusting.

In the treatment of parts of plants, the active compound concentrations in the use forms can be varied within a substantial range. They are, in general, between 1 and 0.0001% by weight, preferably between 0.5 and 0.001%.

In the treatment of seed, amounts of active compound of 0.001 to 50 g per kilogram of seed, preferably 0.01 to 10 g, are generally required.

For the treatment of soil, active compound concentrations of 0.00001 to 0.1% by weight, preferably 0.0001 to 0.02%, are required at the place of action.

PREPARATION EXAMPLES

Example 1

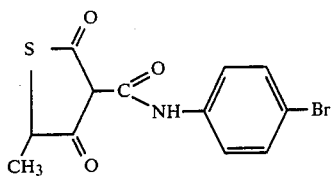

5.1 g (0.025 mole) of ethyl 5-methylthiolane-2,4-dione-3-carboxylate and 4.3 g (0.025 mole) of 4-bromoaniline are boiled under reflux together in 25 ml of toluene for one hour. When the reaction has ended, the mixture is cooled to 0° C., whereupon some of the product crystallizes out. A further fraction is obtained by concentrating the mother liquor and recrystallizing the residue from 30 ml of ethanol.

A total of 7.4 g (90% of theory) of 5-methylthiolane-2,4-dione-3-[N-(4-bromophenyl)]-carboxamide of melting point 130° C. to 134° C. are obtained.

Preparation of the starting compound

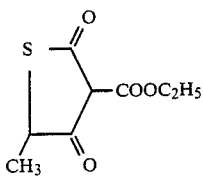

14.4 g (0.05 mole) of diethyl 2-acetylthiopropionyl-malonate are introduced into 50 ml (0.1 mole) of 2N sodium hydroxide solution. The solution which forms is left to stand at room temperature for 30 minutes and then acidified and extracted with ethyl acetate. The combined ethyl acetate phases are dried over sodium sulphate and concentrated in vacuo. The crystalline crude product can be recrystallized from ethanol.

8.6 g (85% of theory) of ethyl 5-methylthiolane-2,4-dione-3-carboxylate of melting point 82° C. to 83° C. are obtained.

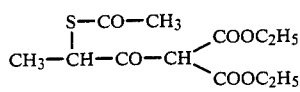

19.2 g (0.12 mole) of diethyl malonate are introduced into a solution of 6.5 g (0.12 mole) of sodium methylate in 100 ml of ethanol. The solvent is removed in vacuo and the residue is dissolved in 100 ml of tetrahydrofuran. 10-g (0.06 mole) of 2-acetylthiopropionyl chloride are added dropwise at 0° C., with stirring, to the solution thus obtained and, when the addition has ended, the mixture is stirred at room temperature for one hour. For working up, the solvent is removed in vacuo, the residue is partitioned in an ethyl acetate/water mixture, the organic phase is separated off and all the volatile constituents are removed under a high vacuum. 14.4 g (82.6% of theory) of crude diethyl 2-acetylthiopropionylmalonate remain as the residue, which can be used for further reactions without subsequent purification.

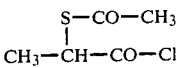

66.2 g (0.52 mole) of oxalyl chloride are added dropwise to 44.3 g (0.3 mole) of 2-acetylthiopropionic acid in 460 ml of dry methylene chloride at room temperature and, when the addition has ended, the mixture is stirred at room temperature until the evolution of gas has ended.

For working up, the solvent and excess oxalyl chloride are removed in vacuo and the residue is distilled under a high vacuum.

22.7 g (45% of theory) of 2-acetylthiopropionyl chloride of boiling point 60° C. under 1.3 mbar are obtained.

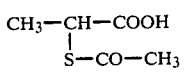

60.7 g (0.6 mole) of triethylamine are added dropwise to 45.9 g (0.3 mole) of 2-bromopropionic acid in 300 ml of tetrahydrofuran at 0° C. with stirring, followed by 22.8 g (0.3 mole) of thioacetic acid. When the addition has ended, stirring is continued at 0° C. for a further 3 hours and then at room temperature for 12 hours. For working up, the solvent is removed in vacuo and the residue is partitioned in a mixture of 300 ml of ethyl acetate and 300 ml of water. The organic phase is separated off, dried with sodium sulphate and freed from the solvent in vacuo.

44.5 g (100% of theory) of 2-acetylthiopropionic acid are obtained, and can be used without further purification.

The following compounds of the general formula (I) are obtained in a corresponding manner and in accordance with the general description of the preparation:

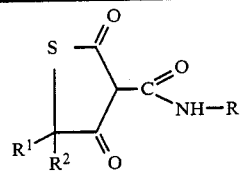

| Example No. | R | R¹ | R² | Melting point [°C.] |
|---|---|---|---|---|
| 2 | phenyl | H | H | 158 |
| 3 | 4-F-phenyl | H | H | 169 |
| 4 | 4-Cl-phenyl | H | H | 214 |
| 5 | 3-Cl-phenyl | H | H | 183 |
| 6 | 4-Br-phenyl | H | H | 213 |

-continued

| # | Ar | R | R' | mp |
|---|----|----|----|----|
| 7 | 4-NC-C₆H₄- | H | H | >220 |
| 8 | 3-NC-C₆H₄- | H | H | 230 |
| 9 | 4-O₂N-C₆H₄- | H | H | 265 |
| 10 | 4-CH₃-C₆H₄- | H | H | 173 |
| 11 | 4-CH₃O-C₆H₄- | H | H | 145 |
| 12 | 3,4-Cl₂-C₆H₃- | H | H | 216 |
| 13 | 2,6-(CH₃)₂-C₆H₃- | H | H | 133 |
| 14 | C₆H₅- | CH₃ | H | 102 |
| 15 | 4-F-C₆H₄- | CH₃ | H | 127 |
| 16 | 4-Cl-C₆H₄- | CH₃ | H | 136 |
| 17 | 3-Cl-C₆H₄- | CH₃ | H | 124 |
| 18 | 2-Cl-C₆H₄- | CH₃ | H | 107 |
| 19 | 4-NC-C₆H₄- | CH₃ | H | 208 |
| 20 | 3-NC-C₆H₄- | CH₃ | H | 157 |
| 21 | 4-CH₃-C₆H₄- | CH₃ | H | 92 |
| 22 | 4-CH₃O-C₆H₄- | CH₃ | H | 93.5 |
| 23 | 4-C₆H₅O-C₆H₄- | CH₃ | H | 90 |
| 24 | 2-(2-CH₃-C₆H₄O)-C₆H₄- | CH₃ | H | 102 |
| 25 | 2,4-Cl₂-C₆H₃- | CH₃ | H | 172 |
| 26 | 3,4-Cl₂-C₆H₃- | CH₃ | H | 156 |
| 27 | 3,5-Cl₂-C₆H₃- | CH₃ | H | 105 |
| 28 | 3,4-(CH₃)(Cl)-C₆H₃- | CH₃ | H | 135 |
| 29 | 3-Cl-4-CH₃-C₆H₃- | CH₃ | H | 106 |
| 30 | 2-Cl-3-CH₃-C₆H₃- | CH₃ | H | 105 |
| 31 | 2-Cl-4-CF₃-C₆H₃- | CH₃ | H | 135 |
| 32 | 2-Cl-5-CF₃-C₆H₃- | CH₃ | H | 137 |
| 33 | 2-CF₃-4-Cl-C₆H₃- | CH₃ | H | 95 |
| 34 | 2-Cl-4-CH₃S-C₆H₃- | CH₃ | H | 141 |
| 35 | 2-CH₃O-3-CH₃-C₆H₃- | CH₃ | H | 101 |
| 36 | 2,6-Cl₂-4-HO-C₆H₂- | CH₃ | H | 177 |

-continued

| # | Ar | R | R' | mp |
|---|---|---|---|---|
| 37 | 4-Cl-2-OCH₃-5-CH₃-C₆H₂ | CH₃ | H | 165 |
| 38 | 4-Cl-2,5-(OCH₃)₂-C₆H₂ | CH₃ | H | 137 |
| 39 | 2,5-Cl₂-4-CN-C₆H₂ | CH₃ | H | 178 |
| 40 | 4-F-C₆H₄ | C₂H₅ | H | 141 |
| 41 | 4-Cl-C₆H₄ | C₂H₅ | H | 154 |
| 42 | 4-Br-C₆H₄ | C₂H₅ | H | 153 |
| 43 | 4-F-C₆H₄ | (CH₃)₂CH— | H | 140 |
| 44 | 4-Cl-C₆H₄ | (CH₃)₂CH— | H | 161 |
| 45 | 3-Cl-C₆H₄ | (CH₃)₂CH— | H | 137 |
| 46 | 4-Br-C₆H₄ | (CH₃)₂CH— | H | 163 |
| 47 | 3-CF₃-C₆H₄ | (CH₃)₂CH— | H | 107 |
| 48 | 4-C₆H₅-C₆H₄ | (CH₃)₂CH— | H | 112 |
| 49 | 4-C₆H₅O-C₆H₄ | (CH₃)₂CH— | H | 106 |
| 50 | 3,4-Cl₂-C₆H₃ | (CH₃)₂CH— | H | 132 |
| 51 | 2,4-Br₂-C₆H₃ | (CH₃)₂CH— | H | 122 |
| 52 | 4-Br-2-Cl-C₆H₃ | (CH₃)₂CH— | H | 128 |
| 53 | 4-Br-2-CH₃-C₆H₃ | (CH₃)₂CH— | H | 149 |
| 54 | 2-Cl-4-CF₃-C₆H₃ | (CH₃)₂CH— | H | 112 |
| 55 | 4-F-C₆H₄ | (CH₃)₃C— | H | 149 |
| 56 | 4-Cl-C₆H₄ | (CH₃)₃C— | H | 168 |
| 57 | 3-Cl-C₆H₄ | (CH₃)₃C— | H | 122 |
| 58 | 4-Br-C₆H₄ | (CH₃)₃C— | H | 160 |
| 59 | 4-CH₃-C₆H₄ | (CH₃)₃C— | H | 155 |
| 60 | 4-(CH₃)₃C-C₆H₄ | (CH₃)₃C— | H | 158 |
| 61 | 4-C₆H₅-C₆H₄ | (CH₃)₃C— | H | 175 |
| 62 | 4-CF₃-C₆H₄ | (CH₃)₃C— | H | 159 |
| 63 | 3-CF₃-C₆H₄ | (CH₃)₃C— | H | 120 |
| 64 | 4-CF₃O-C₆H₄ | (CH₃)₃C— | H | 143 |
| 65 | 4-CF₃S-C₆H₄ | (CH₃)₃C— | H | 177 |
| 66 | 4-C₆H₅-C₆H₄ | (CH)₃C— | H | 133 |
| 67 | 3,5-Cl₂-C₆H₃ | (CH₃)₃C— | H | 75 |
| 68 | 3,4-Br₂-C₆H₃ | (CH₃)₃C— | H | 139 |
| 69 | 3,5-(CF₃)₂-C₆H₃ | (CH₃)₃C— | H | 91 |

| # | Aryl | R | | mp |
|---|---|---|---|---|
| 70 | 4-bromo-2-chlorophenyl | (CH₃)₃C— | H | 110 |
| 71 | 2-bromo-3-methylphenyl | (CH₃)₃C— | H | 136 |
| 72 | 2-chloro-4-(trifluoromethyl)phenyl | (CH₃)₃C— | H | 127 |
| 73 | 4-chloro-2-(trifluoromethyl)phenyl | (CH₃)₃C— | H | 104 |
| 74 | 2-chloro-4-(methylthio)phenyl | (CH₃)₃C— | H | 142 |
| 75 | 2-chloro-4-(trifluoromethoxy)phenyl | (CH₃)₃C— | H | 143 |
| 76 | 2-methyl-6-(2-chloro-1,1,2-trifluoroethoxy... dioxole)phenyl | (CH₃)₃C— | H | 129 |
| 77 | C₆H₅— | C₆H₅— | H | 175 |
| 78 | 4-Cl-C₆H₄— | C₆H₅— | H | 228 |
| 79 | 4-CH₃-C₆H₄— | C₆H₅— | H | 181 |
| 80 | 4-CH₃O-C₆H₄— | C₆H₅— | H | 180 |
| 81 | C₆H₅— | cyclohexyl-CH₂— | H | 135 |
| 82 | 4-Cl-C₆H₄— | cyclohexyl-CH₂— | H | 185 |
| 83 | 4-Br-C₆H₄— | cyclohexyl-CH₂— | H | 199–201 |
| 84 | 4-CH₃-C₆H₄— | cyclohexyl-CH₂— | H | 128–130 |
| 85 | 4-C₂H₅-C₆H₄— | cyclohexyl-CH₂— | H | 105–106 |
| 86 | 4-(CH₃)₃C-C₆H₄— | cyclohexyl-CH₂— | H | 141–143 |
| 87 | 4-C₆H₅-C₆H₄— | cyclohexyl-CH₂— | H | 130 |
| 88 | 4-F₃C-C₆H₄— | cyclohexyl-CH₂— | H | 175 |
| 89 | 3-F₃C-C₆H₄— | cyclohexyl-CH₂— | H | 109–110 |
| 90 | 4-F₃CO-C₆H₄— | cyclohexyl-CH₂— | H | 144–147 |
| 91 | 4-F₃CS-C₆H₄— | cyclohexyl-CH₂— | H | 167–168 |
| 92 | 2,4-dichlorophenyl | cyclohexyl-CH₂— | H | 119–122 |
| 93 | 2-chloro-4-(trifluoromethyl)phenyl | cyclohexyl-CH₂— | H | 147 |
| 94 | 4-chloro-2-(trifluoromethyl)phenyl | cyclohexyl-CH₂— | H | 130–133 |
| 95 | 4-CF₃O-C₆H₄— | CH₃ | H | 136 |
| 96 | 4-CF₃O-C₆H₄— | H | H | 166 |
| 97 | 4-CF₃O-C₆H₄— | (CH₃)₂CH— | H | 135–37 |
| 98 | 4-CF₃O-C₆H₄— | C₂H₅ | H | 143–44 |
| 99 | 3,4-dimethylphenyl | CH₃ | H | 88–90 |
| 100 | 4-i-C₃H₇-C₆H₄— | CH₃ | H | 85–86 |
| 101 | 2-CH₃-C₆H₄— | CH₃ | H | 107–08 |
| 102 | 4-CF₃-C₆H₄— | CH₃ | H | 152–53 |

| # | Ar | R | R' | mp (°C) |
|---|---|---|---|---|
| 103 | 2-CF₃-C₆H₄- | CH₃ | H | 91 |
| 104 | 3,4-Br₂-C₆H₃- | CH₃ | H | 197-98 |
| 105 | 3-Cl-4-Br-C₆H₃- | CH₃ | H | 170-71 |
| 106 | 4-C₂H₅-C₆H₄- | CH₃ | H | 89-90 |
| 107 | 4-(CH₃)₃C-C₆H₄- | CH₃ | H | 119 |
| 108 | 4-C₆H₅-C₆H₄- | CH₃ | H | 133-34 |
| 109 | 4-C₂H₅O-3-Cl-C₆H₃- | CH₃ | H | Oil |
| 110 | 3-CH₃-4-(unspec)-C₆H₃- | CH₃ | H | Oil |
| 111 | 4-Br-C₆H₄- | n-C₃H₇- | H | 142-44 |
| 112 | 4-C₂H₅-C₆H₄- | n-C₃H₇- | H | 102-03 |
| 113 | 4-i-C₃H₇-C₆H₄- | n-C₃H₇- | H | 97-98 |
| 114 | 4-(CH₃)₃C-C₆H₄- | n-C₃H₇- | H | 80-83 |
| 115 | 3-Cl-4-CH₃-C₆H₃- | n-C₃H₇- | H | 96-97 |
| 116 | 4-n-C₄H₉-C₆H₄- | n-C₃H₇- | H | 94-95 |
| 117 | 4-CH₃(CH₂)₇-C₆H₄- | n-C₃H₇- | H | 82-83 |
| 118 | 4-CH₃(CH₂)₉-C₆H₄- | n-C₃H₇- | H | 87-88 |
| 119 | 4-CH₃(CH₂)₁₁-C₆H₄- | n-C₃H₇- | H | 72-74 |
| 120 | 4-CH₃(CH₂)₁₃-C₆H₄- | n-C₃H₇- | H | 73-74 |
| 121 | 4-CH₃-C₆H₄- | n-C₃H₇- | H | 104 |
| 122 | 4-CF₃-C₆H₄- | n-C₃H₇- | H | 156-58 |
| 123 | C₆H₅- | n-C₃H₇- | H | 105-06 |
| 124 | 4-Cl-C₆H₄- | n-C₃H₇- | H | 133-34 |
| 125 | 4-F-C₆H₄- | n-C₃H₇- | H | 131-33 |
| 126 | 4-cyclohexyl-C₆H₄- | n-C₃H₇- | H | 129-30 |
| 127 | 4-C₆H₅-C₆H₄- | n-C₃H₇- | H | Oil |
| 128 | 4-CH₃O-C₆H₄- | n-C₃H₇- | H | 114-15 |
| 129 | 4-C₂H₅O-C₆H₄- | n-C₃H₇- | H | 108-09 |
| 130 | 4-C₆H₅O-C₆H₄- | n-C₃H₇- | H | 109-11 |
| 131 | 4-CF₃S-C₆H₄- | n-C₃H₇- | H | 177-79 |
| 132 | 4-NC-C₆H₄- | n-C₃H₇- | H | Oil |
| 133 | 2-Br-C₆H₄- | n-C₃H₇- | H | Oil |
| 134 | 3-Cl-4-Br-C₆H₃- | n-C₃H₇- | H | 123 |
| 135 | 2-Cl-C₆H₄- | n-C₃H₇- | H | 90-92 |
| 136 | 3-Cl-C₆H₄- | n-C₃H₇- | H | 133-34 |
| 137 | 3,4-Cl₂-C₆H₃- | n-C₃H₇- | H | 112-13 |
| 138 | 2,3-Cl₂-C₆H₃- | n-C₃H₇- | H | 124-27 |
| 139 | 2,4-Cl₂-C₆H₃- | n-C₃H₇- | H | 128-29 |

| No. | Ar | R | R' | mp (°C) |
|---|---|---|---|---|
| 140 | 3,5-di-Cl-C₆H₃ | n-C₃H₇— | H | 154–56 |
| 141 | 2,3-di-CH₃-C₆H₃ | n-C₃H₇— | H | 94–96 |
| 142 | 2,6-di-CH₃-C₆H₃ | n-C₃H₇— | H | 76–78 |
| 143 | 2,3-di-CH₃-C₆H₃ (CH₃ at 2,3) | n-C₃H₇— | H | 95–96 |
| 144 | 3,5-di-CH₃-C₆H₃ | n-C₃H₇— | H | 100–01 |
| 145 | 2,5-di-CH₃-C₆H₃ | n-C₃H₇— | H | 103–04 |
| 146 | 3,5-di-CF₃-C₆H₃ | n-C₃H₇— | H | 93–95 |
| 147 | 2-i-C₃H₇-C₆H₄ | n-C₃H₇— | H | Oil |
| 148 | 2,4,5-tri-CH₃-C₆H₂ | n-C₃H₇— | H | 108–09 |
| 149 | 2-OCH₃-C₆H₄ | n-C₃H₇— | H | 104–05 |
| 150 | 3-CH₃O-C₆H₄ | n-C₃H₇— | H | 70–72 |
| 151 | 3-C₂H₅O-C₆H₄ | n-C₃H₇— | H | 76–77 |
| 152 | 2-C₂H₅-C₆H₄ | n-C₃H₇— | H | 54–58 |
| 153 | 3-CH₃-C₆H₄ | n-C₃H₇— | H | 73–74 |
| 154 | 3-CF₃-C₆H₄ | n-C₃H₇— | H | 98–99 |
| 155 | 4-CF₃O-C₆H₄ | n-C₃H₇— | H | 149–50 |
| 156 | 2-CH₃-C₆H₄ | n-C₃H₇— | H | 99–100 |
| 157 | 4-NO₂-C₆H₄ | n-C₃H₇— | H | 194–97 |
| 158 | 3-Cl-4-CF₃-C₆H₃ | n-C₃H₇— | H | 145–47 |
| 159 | 2-CF₃-4-Cl-C₆H₃ | n-C₃H₇— | H | 79–82 |
| 160 | 2-Cl-4-CF₃-C₆H₃ | n-C₃H₇— | H | 100–01 |
| 161 | 2,3-di-Br-C₆H₃ | n-C₃H₇— | H | 129–31 |
| 162 | 2-Cl-3-CH₃-C₆H₃ | n-C₃H₇— | H | 105–06 |
| 163 | 2-CH₃-4-Cl-C₆H₃ | n-C₃H₇— | H | Oil |
| 164 | —(CH₂)₁₁—CH₃ | H | H | NMR: 3,35 O=CH—NH—CH₂ |
| 165 | 3-Cl-5-CH₃-C₆H₃ | —(CH₂)₂—CH₃ | H | 99 |
| 166 | 2-CH₃-4-Cl-C₆H₃ | —(CH₂)₂—CH₃ | H | 93–94 |
| 167 | 2-Cl-5-CF₃-C₆H₃ | —(CH₂)₂—CH₃ | H | 149–150 |

-continued
| | | | | |
|---|---|---|---|---|
| 168 | 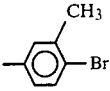 2-Br, 4-CH₃ | —(CH₂)₂—CH₃ | H | 107–108 |
| 169 | 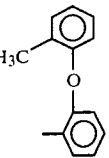 2-CF₃, 4-Cl | —(CH₂)₂—CH₃ | H | 87 |
| 170 | 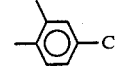 2-Cl, 3-OCH₃ | —(CH₂)₂—CH₃ | H | 145–147 |
| 171 | 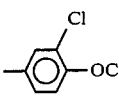 4-H₃CO, 2-Cl, 5-CH₃ | —(CH₂)₂—CH₃ | H | 137–139 |
| 172 | 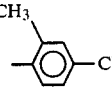 3-OCH₃, 4-Cl, 5-OCH₃ | —(CH₂)₂—CH₃ | H | 101–103 |
| 173 | 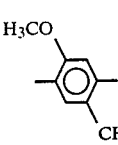 2-Cl, 3-SCH₃ | —(CH₂)₂—CH₃ | H | 146–148 |
| 174 | 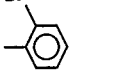 2-Br | H | H | 183–184 |
| 175 | 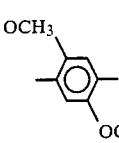 2-Cl, 4-Br | H | H | 205–206 |
| 176 | 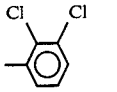 3-CN | —(CH₂)₂—CH₃ | H | NMR: 4.3 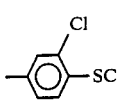 |
| 177 | 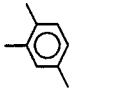 2,5-Cl, 4-CN | —(CH₂)₂—CH₃ | H | 190 |
| 178 | 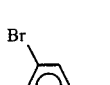 2-Cl | H | H | 168–169 |
| 179 | 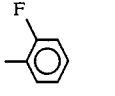 2-OCH₃, 4-CH₃ | —(CH₂)₂—CH₃ | H | 75–76 |
| 180 | 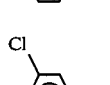 naphthyl | —(CH₂)₂—CH₃ | H | 120–121 |
| 181 | 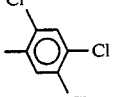 2-CH₃, 4-cyclohexyl | —(CH₂)₂—CH₃ | H | 105 |
| 182 | 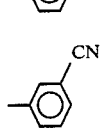 2-(2-methylphenoxy), 3-CH₃ | —(CH₂)₂—CH₃ | H | 78 |
| 183 | 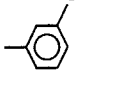 2,4-CH₃ | CH₃ | H | 92–93 |
| 184 | 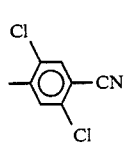 2-Br | CH₃ | H | 121–122 |
| 185 | 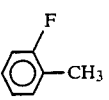 2,3-Cl | CH₃ | H | 148–149 |
| 186 | 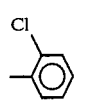 2,5-Cl | CH₃ | H | 182–183 |
| 187 | 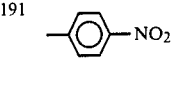 2-F | CH₃ | H | 73–75 |
| 188 | 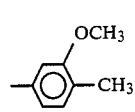 2,3,4-Cl | CH₃ | H | 207–209 |
| 189 | 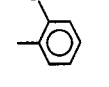 3-F | CH₃ | H | 138–139 |
| 190 |  2-F, 4-CH₃ | CH₃ | H | 135–136 |
| 191 | 4-NO₂ | CH₃ | H | 223 |
| 192 | 2-NO₂ | CH₃ | H | 131 |
| 193 | 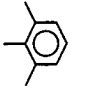 2,3-Cl | CH₃ | H | 172–174 |
| 194 | 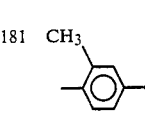 2-Cl, 3-CH₃ | CH₃ | H | 148–149 |

| | | | | |
|---|---|---|---|---|
| 195 | 2,4-(CH₃)₂-C₆H₃ | CH₃ | H | 137–138 |
| 196 | 3,5-(CF₃)₂-C₆H₃ | CH₃ | H | 131–133 |
| 197 | 3,5-(CH₃)₂-C₆H₃ | CH₃ | H | 105–106 |
| 198 | 2-(CH₃)₂CH-C₆H₄ | CH₃ | H | 72–73 |
| 199 | 2-CH₃-6-C₂H₅-C₆H₃ | CH₃ | H | 73–75 |
| 200 | 2,4,5-(CH₃)₃-C₆H₂ | CH₃ | H | 110–112 |
| 201 | 2,4,6-(CH₃)₃-C₆H₂ | CH₃ | H | 87–88 |
| 202 | 2,6-(C₂H₅)₂-C₆H₃ | CH₃ | H | 82–83 |
| 203 | 2,4-(CH₃)₂-6-C₂H₅-C₆H₂ | CH₃ | H | 64–67 |
| 204 | 2,6-(C₂H₅)₂-4-CH₃-C₆H₂ | CH₃ | H | 70–72 |
| 205 | 2,6-((CH₃)₂CH)₂-C₆H₃ | CH₃ | H | 126–127 |
| 206 | 3-CH₃-C₆H₄ | CH₃ | H | 79–80 |
| 207 | 2-C₂H₅-C₆H₄ | CH₃ | H NMR: 414 | (–CH(S)–CHO) |
| 208 | 4-(CH₂)₃CH₃-C₆H₄ | CH₃ | H | 66–68 |
| 209 | 4-(CH₂)₂CH₃-C₆H₄ | CH₃ | H | 84–85 |
| 210 | 4-(CH₂)₇CH₃-C₆H₄ | CH₃ | H | 67 |
| 211 | 4-(CH₂)₉CH₃-C₆H₄ | CH₃ | H | 65–67 |
| 212 | 4-(CH₂)ₘCH₃-C₆H₄ | CH₃ | H | 69 |
| 213 | 4-(CH₂)₁₃CH₃-C₆H₄ | CH₃ | H | 72–73 |
| 214 | 2,3-(CH₃)₂-C₆H₃ | CH₃ | H | 122 |
| 215 | 2,3,6-(CH₃)₃-C₆H₂ | CH₃ | H | 132–134 |
| 216 | 4-cyclohexyl-C₆H₄ | CH₃ | H | 135–137 |
| 217 | 2-CH₃-4-cyclohexyl-C₆H₃ | CH₃ | H | 93–95 |
| 218 | 2,3-Cl₂-C₆H₃ | H | H | 190 |
| 219 | 1-naphthyl | CH₃ | H | 128–129 |
| 220 | 2-OCH₃-C₆H₄ | CH₃ | H | 98–99 |
| 221 | 4-CH₃-C₆H₄ | C₂H₅ | H | 95–97 |
| 222 | 2,6-((CH₂)₂CH₃)₂-C₆H₃ | C₂H₅ | H NMR: 4,1 | (–CH(S)–CHO) |

-continued
| | | | | |
|---|---|---|---|---|
| 223 | 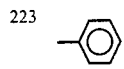 | C$_2$H$_5$ | H | 109–110 |
| 224 | 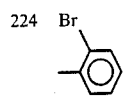 | C$_2$H$_5$ | H | 119–120 |
| 225 | 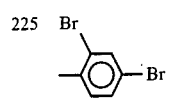 | C$_2$H$_5$ | H | 150–151 |
| 226 | 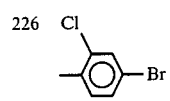 | C$_2$H$_5$ | H | 144 |
| 227 | 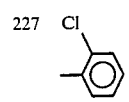 | C$_2$H$_5$ | H | 119 |
| 228 | 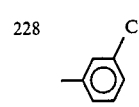 | C$_2$H$_5$ | H | 119 |
| 229 | 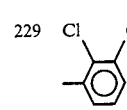 | C$_2$H$_5$ | H | 123 |
| 230 | 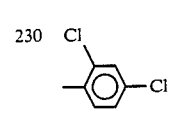 | C$_2$H$_5$ | H | 150–151 |
| 231 | 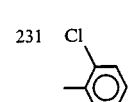 | C$_2$H$_5$ | H | 126 |
| 232 | 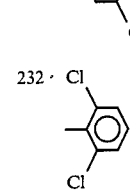 | C$_2$H$_5$ | H | 152 |
| 233 | 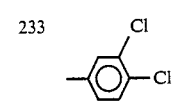 | C$_2$H$_5$ | H | 155 |
| 234 | 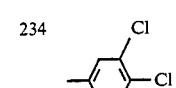 | C$_2$H$_5$ | H | 154 |
| 235 | 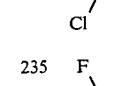 | C$_2$H$_5$ | H | 112 |
| 236 | 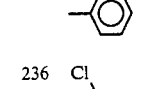 | H | H | 206–208 |
| 237 | 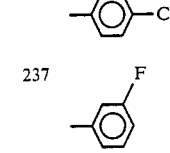 | C$_2$H$_5$ | H | 151 |
-continued
| | | | | |
|---|---|---|---|---|
| 238 |  | C$_2$H$_5$ | H | 116 |
| 239 | 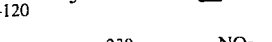 | C$_2$H$_5$ | H | 112–115 |
| 240 | 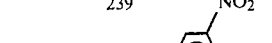 | C$_2$H$_5$ | H | 198–200 |
| 241 |  | C$_2$H$_5$ | H | 108 |
| 242 | 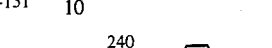 | C$_2$H$_5$ | H | 163 |
| 243 | 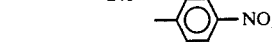 | C$_2$H$_5$ | H | 145 |
| 244 |  | C$_2$H$_5$ | H | 136–138 |
| 245 | 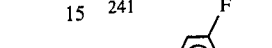 | C$_2$H$_5$ | H | 156 |
| 246 |  | C$_2$H$_5$ | H | 140 |
| 247 | 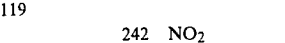 | C$_2$H$_5$ | H | 104 |
| 248 |  | C$_2$H$_5$ | H | 122 |
| 249 |  | C$_2$H$_5$ | H | 134 |
| 250 |  | C$_2$H$_5$ | H | 135 |
| 251 |  | C$_2$H$_5$ | H | 127 |

-continued
| | | | | |
|---|---|---|---|---|
| 252 | 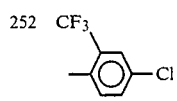 | C₂H₅ | H | 128 |
| 253 | 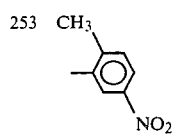 | C₂H₅ | H | 147 |
| 254 | 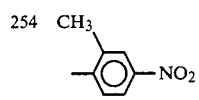 | C₂H₅ | H | 112 |
| 255 | 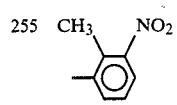 | C₂H₅ | H | 127 |
| 256 | 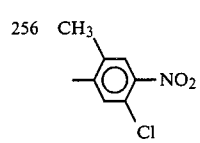 | C₂H₅ | H | 103 |
| 257 | 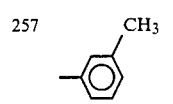 | C₂H₅ | H | 95 |
| 258 | 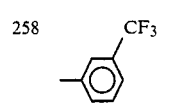 | C₂H₅ | H | 100 |
| 259 | 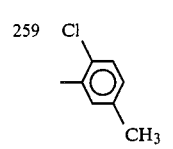 | C₂H₅ | H | 95 |
| 260 | 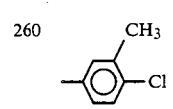 | C₂H₅ | H | 112 |
| 261 | 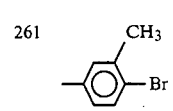 | C₂H₅ | H | 115 |
| 262 | 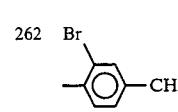 | C₂H₅ | H | 108 |
| 263 | 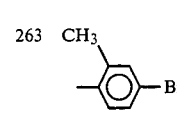 | C₂H₅ | H | 128 |
| 264 | 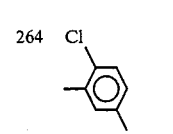 | C₂H₅ | H | 110 |
| 265 | 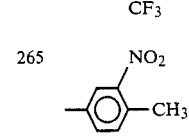 | C₂H₅ | H | 145 |
| 266 | 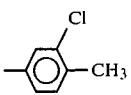 | C₂H₅ | H | 120 |
| 267 | 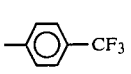 | C₂H₅ | H | 141 |
| 268 | 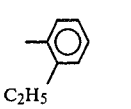 | C₂H₅ | H | 70 |
| 269 | 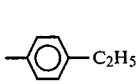 | C₂H₅ | H | 92 |
| 270 | 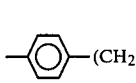 | C₂H₅ | H | 87 |
| 271 | 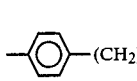 | C₂H₅ | H | 82 |
| 272 | 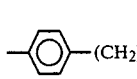 | C₂H₅ | H | 80 |
| 273 | 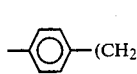 | C₂H₅ | H | 77 |
| 274 | 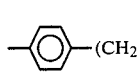 | C₂H₅ | H | 75 |
| 275 | 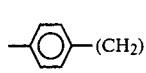 | C₂H₅ | H | 30 |
| 276 | 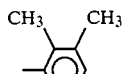 | C₂H₅ | H | 110 |
| 277 | 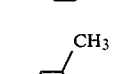 | C₂H₅ | H | 86 |
| 278 | 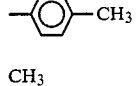 | C₂H₅ | H | 137 |
| 279 | 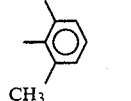 | C₂H₅ | H | 92 |
| 280 | 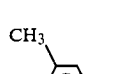 | C₂H₅ | H | 100 |
| 281 | 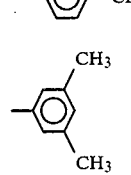 | C₂H₅ | H | 105 |

| | | | | |
|---|---|---|---|---|
| 282 | 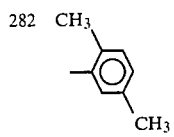 | C₂H₅ | H | 96 |
| 283 | 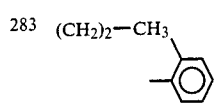 (CH₂)₂—CH₃ | C₂H₅ | H | 56 |
| 284 | 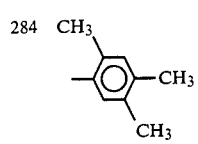 | C₂H₅ | H | 106 |
| 285 | 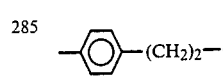 —(CH₂)₂—CH₃ | C₂H₅ | H | 78 |
| 286 | 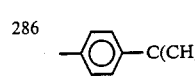 —C(CH₃)₃ | C₂H₅ | H | 98 |
| 287 | 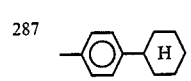 | C₂H₅ | H | 99 |
| 288 | 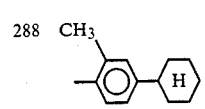 | C₂H₅ | H | 134 |
| 289 | 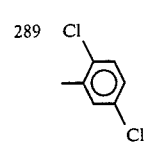 | H | H | 234–235 |
| 290 | 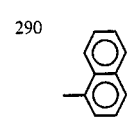 | C₂H₅ | H | 93 |
| 291 | 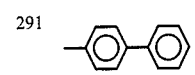 | C₂H₅ | H | 131 |
| 292 | 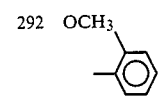 | C₂H₅ | H | 120 |
| 293 | 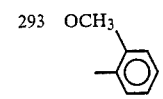 | CH₃ | H | 115–116 |
| 294 | 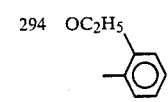 | CH₃ | H | 103–104 |
| 295 | 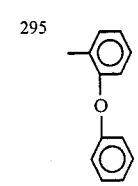 | CH₃ | H | 132–133 |
| 296 | 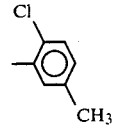 | CH₃ | H | 128–129 |
| 297 | 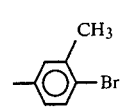 | CH₃ | H | 118–119 |
| 298 | 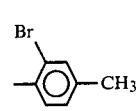 | CH₃ | H | 148–149 |
| 299 | 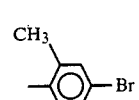 | CH₃ | H | 117–118 |
| 300 | 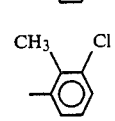 | CH₃ | H | 138–139 |
| 301 | 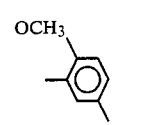 | CH₃ | H | 113–114 |
| 302 | 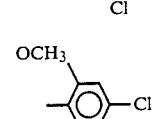 | CH₃ | H | 201–204 |
| 303 | 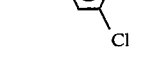 | CH₃ | H | 180 |
| 304 | 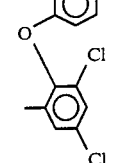 | CH₃ | H | 220 |
| 305 | 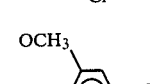 | CH₃ | H | 65–66 |
| 306 | 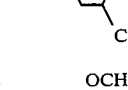 | CH₃ | H | 198–200 |
| 307 | 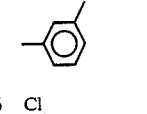 | CH₃ | H | 168 |
| 308 | 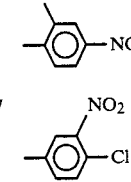 | CH₃ | H | 212–215 |

-continued
| No. | Ar | R | R' | mp (°C) |
|---|---|---|---|---|
| 309 |  | CH₃ | H | 164 |
| 310 | 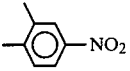 | CH₃ | H | 215 |
| 311 | 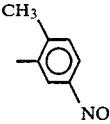 | CH₃ | 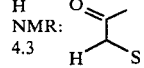 NMR: 4.3 | |
| 312 | 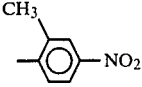 | CH₃ | H | 189 |
| 313 |  | CH₃ | H | 158 |
| 314 | 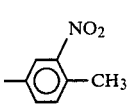 | CH₃ | H | 138–140 |
| 315 | 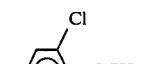 | CH₃ | H | 152–153 |
| 316 | 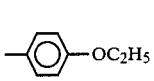 | CH₃ | H | 136–138 |
| 317 | 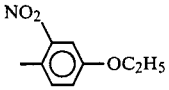 | CH₃ | H | 121–123 |
| 318 | 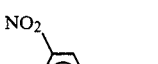 | CH₃ | H | 149–153 |
| 319 |  | CH₃ | H | 115–116 |
| 320 |  | CH₃ | H | 93–95 |
| 321 | 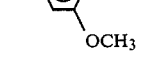 | CH₃ | H | 115–116 |
| 322 | 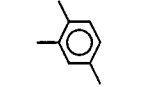 | CH₃ | H | 89–90 |
| 323 | 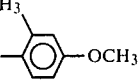 | CH₃ | H | 122 |
| 324 | 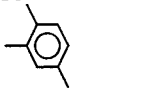 | CH₃ | H | 96–97 |
| 325 | 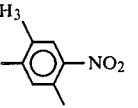 | CH₃ | H | 193–195 |
| 326 | 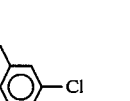 | CH₃ | H | 117–119 |
| 327 | 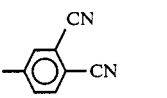 | CH₃ | H | 213–214 |
| 328 |  | H | H | 124–125 |
| 329 |  | H | H | 141–142 |
| 330 | 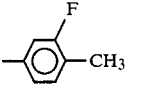 | H | H | 164–166 |
| 331 | 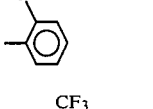 | H | H | 136–137 |
| 332 | 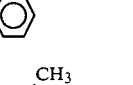 | H | H | 156–158 |
| 333 | 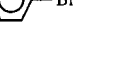 | H | H | 197–200 |
| 334 |  | H | H | 165–166 |
| 335 |  | H | H | 181–183 |
| 336 | 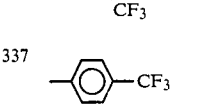 | H | H | 162–163 |
| 337 |  | H | H | 117–118 |

| No. | Ar | R2 | R3 | mp (°C) |
|---|---|---|---|---|
| 338 | 2-ethylphenyl (C2H5) | H | H | 138–139 |
| 339 | 3-chloro-4-methylphenyl | H | H | 214–215 |
| 340 | 2-chloro-3-methylphenyl | H | H | 183–184 |
| 341 | 4-chloro-2-(CF3)phenyl | H | H | 116–117 |
| 342 | 2-chloro-3-methylphenyl (Cl top, CH3 bottom) | H | H | 164 |
| 343 | 3-chloro-5-methylphenyl | H | H | 187–188 |
| 344 | 4-chloro-2-methylphenyl | H | H | 192 |
| 345 | 3-chloro-4-methylphenyl (Cl, CH3) | H | H | 169–171 |
| 346 | 3,4-dimethylphenyl | H | H | 163–164 |
| 347 | 2,4-dimethylphenyl | H | H | 160–161 |
| 348 | 2,6-dimethylphenyl | H | H | 183–184 |
| 349 | 3,5-dimethylphenyl | H | H | 213–214 |
| 350 | 3,5-bis(CF3)phenyl | H | H | 154–155 |
| 351 | 3,4-dimethylphenyl | H | H | 200–201 |
| 352 | 3-chloro-4-bromophenyl | phenyl | H | 208–210 |
| 353 | 2-isopropylphenyl | H | H | 132–133 |
| 354 | 2-ethyl-3-methylphenyl | H | H | 94–95 |
| 355 | 2,4,6-trimethylphenyl | H | H | 167–169 |
| 356 | 4-isopropylphenyl | H | H | 92–93 |
| 357 | 4-tert-butylphenyl | H | H | 128–129 |
| 358 | 2,6-diethylphenyl | H | H | 86–87 |
| 359 | 2,3-dimethylphenyl | H | H | 160–161 |
| 360 | 2-ethylphenyl | C2H5 | H | 82 |
| 361 | 2-phenoxyphenyl | C2H5 | H | 151 |
| 362 | 2-(2-methylphenoxy)phenyl | C2H5 | H | 89 |
| 363 | 4-chloro-2-methoxyphenyl | C2H5 | H | 116 |

| No. | Ar | R | R' | mp (°C) |
|---|---|---|---|---|
| 364 | 3-OCH₃-4,5-diCl-phenyl | C₂H₅ | H | 180 |
| 365 | 2,4-diCl-phenyl (with OPh) | C₂H₅ | H | 175 |
| 366 | 3-OCH₃-4-CH₃-5-NO₂-6-Cl-phenyl | C₂H₅ | H | 188 |
| 367 | 3-OCH₃-phenyl | C₂H₅ | H | 74 |
| 368 | 3-OC₂H₅-phenyl | C₂H₅ | H | 79 |
| 369 | 4-OCH₃-phenyl | C₂H₅ | H | 120 |
| 370 | 4-OC₂H₅-phenyl | C₂H₅ | H | 105 |
| 371 | 3-Cl-4-OCH₃-phenyl | C₂H₅ | H | 120 |
| 372 | 3-Cl-4-SCH₃-phenyl | C₂H₅ | H | 150 |
| 373 | 3-CH₃-4-OCH₃-phenyl | C₂H₅ | H | 90 |
| 374 | 2-CH₃-4-OCH₃-phenyl | C₂H₅ | H | 95 |
| 375 | 2-CH₃-5-OCH₃-phenyl | C₂H₅ | H | 100 |
| 376 | 2-OC₂H₅-5-CH₃-phenyl | C₂H₅ | H | 90 |
| 377 | 2-OCH₃-5-CH₃-phenyl | C₂H₅ | H | 95 |
| 378 | 2-OCH₃-4-Cl-5-CH₃-phenyl | C₂H₅ | H | 121 |
| 379 | 2-OCH₃-4-NO₂-5-CH₃-phenyl | C₂H₅ | H | 166 |
| 380 | 2-OCH₃-5-OCH₃-phenyl | C₂H₅ | H | 110 |
| 381 | 2-OCH₃-4-OCH₃-phenyl | C₂H₅ | H | 90 |
| 382 | 2-OCH₃-4-Cl-5-OCH₃-phenyl | C₂H₅ | H | 130 |
| 383 | 3-CN-phenyl | C₂H₅ | H | 130 |
| 384 | 4-CN-phenyl | C₂H₅ | H | 192 |
| 385 | 3,4-diCN-phenyl | C₂H₅ | H | 188 |
| 386 | 4-phenoxyphenyl | C₂H₅ | H | 98 |
| 387 | 3,4-diCl-phenyl | C₆H₅ | H | 195 |
| 388 | 3,5-diCl-phenyl | C₆H₅ | H | 185 |
| 389 | 4-(CH₂)₃CH₃-phenyl | H | H | 110–112 |
| 390 | 4-(CH₂)₂CH₃-phenyl | H | H | 117–119 |
| 391 | 4-(CH₂)₇CH₃-phenyl | H | H | 85 |

| No. | Ar | R | R' | m.p. (°C) |
|---|---|---|---|---|
| 392 | 4-(CH₂)₉CH₃-C₆H₄- | H | H | 90-92 |
| 393 | 4-(CH₂)₁₁CH₃-C₆H₄- | H | H | 91-92 |
| 394 | 4-(CH₂)₁₃CH₃-C₆H₄- | H | H | 87-89 |
| 395 | 2-OCH₃-C₆H₄- | H | H | 163-164 |
| 396 | 2-OC₂H₅-C₆H₄- | H | H | 129-130 |
| 397 | 2-(C₆H₅O)-C₆H₄- | H | H | 225-226 |
| 398 | 3-OCH₃-C₆H₄- | H | H | 181-182 |
| 399 | 3-OC₂H₅-C₆H₄- | H | H | 148-149 |
| 400 | 4-OC₂H₅-C₆H₄- | H | H | 143-144 |
| 401 | 3-OCH₃-4-CH₃-C₆H₃- | H | H | 169-171 |
| 402 | 3-OC₂H₅-4-CH₃-C₆H₃- | H | H | 166-167 |
| 403 | 3,5-(OCH₃)₂-C₆H₃- | H | H | 180-181 |
| 404 | 2,5-(OCH₃)₂-C₆H₃- | H | H | 156-157 |
| 405 | 2-OCH₃-3-Cl-5-OCH₃-C₆H₂- | H | H | 188-189 |
| 406 | 2-cyclohexyl-C₆H₄- | H | H | 154-155 |
| 407 | 2-Cl-4-SCH₃-C₆H₃- | H | H | 197-198 |
| 408 | 2-CH₃-4-OCH₃-C₆H₃- | H | H | 159-160 |
| 409 | 2-OCH₃-4-CH₃-C₆H₃- | H | H | 145-147 |
| 410 | 2-OCH₃-4-Cl-5-CH₃-C₆H₂- | H | H | 206 |
| 411 | 2-Cl-4-OCH₃-C₆H₃- | H | H | 178-182 |
| 412 | 2-C₂H₅-4-CH₃-6-CH₂-C₆H₂- | H | H | 98-99 |
| 413 | 2-C₂H₅-4-CH₃-6-C₂H₅-C₆H₂- | H | H | 98-99 |
| 414 | 2,6-(CH(CH₃)₂)₂-C₆H₃- | H | H | 144-145 |
| 415 | 2-OCH₃-4-Cl-C₆H₃- | H | H | 203-204 |
| 416 | 2-CH₃-6-(C₆H₅O)-C₆H₃- | H | H | 180-181 |
| 417 | 2-Cl-C₆H₄- | CH₃(CH₂)₃— | H | 94-95 |
| 418 | 4-Br-C₆H₄- | CH₃(CH₂)₃— | H | 160-161 |
| 419 | 2-Cl-C₆H₄- | CH₃(CH₂)₃— | H | 98 |

| No. | Aryl | R | R' | mp (°C) |
|---|---|---|---|---|
| 420 | 4-Cl-C6H4 | CH3(CH2)3— | H | 150-151 |
| 421 | 2,3-Cl2-C6H3 | CH3(CH2)3— | H | 112 |
| 422 | 2,4-Cl2-C6H3 | CH3(CH2)3— | H | 112-113 |
| 423 | 2,5-Cl2-C6H3 | CH3(CH2)3— | H | 125-126 |
| 424 | 3,5-Cl2-C6H3 | CH3(CH2)3— | H | 121 |
| 425 | 3,4-Cl2-C6H3 | CH3(CH2)3— | H | 123-124 |
| 426 | 2-F-C6H4 | CH3(CH2)3— | H | 116-118 |
| 427 | 3-F-C6H4 | CH3(CH2)3— | H | 118-119 |
| 428 | 4-F-C6H4 | CH3(CH2)3— | H | 123-125 |
| 429 | 2-F-4-CH3-C6H3 | CH3(CH2)3— | H | 138-139 |
| 430 | 2-CH3-3-Cl-C6H3 | CH3(CH2)3— | H | 81-83 |
| 431 | 2-CH3-4-Cl-C6H3 | CH3(CH2)3— | H | 105-106 |
| 432 | 2-Br-C6H4 | CH3(CH2)3— | H | 85-86 |
| 433 | 2-CH3-3-Cl-C6H3 | CH3(CH2)3— | H | 87-89 |
| 434 | 2-CF3-4-Cl-C6H3 | CH3(CH2)3— | H | 84-85 |
| 435 | 2-CH3-C6H4 | CH3(CH2)3— | H | 65 |
| 436 | 3-CF3-C6H4 | CH3(CH2)3— | H | 99-100 |
| 437 | 2-Cl-4-CH3-C6H3 | CH3(CH2)3— | H | 117-118 |
| 438 | 2-CH3-3-Cl-C6H3 | CH3(CH2)3— | H | 91-92 |
| 439 | 2-CH3-3-Br-C6H3 | (CH3(CH2)3)— | H | 85-87 |
| 440 | 2-Br-4-CH3-C6H3 | CH3(CH2)3— | H | 90-92 |
| 441 | 2-CH3-4-Br-C6H3 | CH3(CH2)3— | H | 113-114 |
| 442 | 2-Cl-4-CF3-C6H3 | CH3(CH2)3— | H | 79-80 |
| 443 | 4-CH3-C6H4 | CH3(CH2)3— | H | 117 |
| 444 | 2-Cl-4-CH3-C6H3 | CH3(CH2)3— | H | 105-106 |
| 445 | 2-C2H5-C6H4 | CH3(CH2)3— | H | 63-65 |
| 446 | 4-C2H5-C6H4 | CH3(CH2)3— | H | 97-99 |
| 447 | 4-(CH2)3CH3-C6H4 | CH3(CH2)3— | H | 90 |
| 448 | 4-(CH2)2CH3-C6H4 | CH3(CH2)3— | H | 94 |
| 449 | 2,3-(CH3)2-C6H3 | CH3(CH2)3— | H | 73-75 |

-continued

| No. | Ar | R | R' | mp (°C) |
|---|---|---|---|---|
| 450 | 2,4-(CH₃)₂-C₆H₃ | CH₃(CH₂)₃— | H | 68–70 |
| 451 | 2,3-(CH₃)₂-C₆H₃ | CH₃(CH₂)₃— | H | 74–75 |
| 452 | 2,5-(CH₃)₂-C₆H₃ | CH₃(CH₂)₃— | H | 98–99 |
| 453 | 2,6-(CH₃)₂-C₆H₃ (3,5-dimethyl) | CH₃(CH₂)₃— | H | 94–95 |
| 454 | 3,5-(CF₃)₂-C₆H₃ | CH₃(CH₂)₃— | H | 95–96 |
| 455 | 3,4-(CH₃)₂-C₆H₃ | CH₃(CH₂)₃— | H | 101 |
| 456 | 2-CH(CH₃)₂-C₆H₄ | CH₃(CH₂)₃— | H | 59–60 |
| 457 | 4-(CH₂)₇CH₃-C₆H₄ | CH₃(CH₂)₃— | H | 90–91 |
| 458 | 4-(CH₂)₉CH₃-C₆H₄ | CH₃(CH₂)₃— | H | 90–91 |
| 459 | 4-(CH₂)₁₁CH₃-C₆H₄ | CH₃(CH₂)₃— | H | 87–88 |
| 460 | 4-(CH₂)₁₃CH₃-C₆H₄ | CH₃(CH₂)₃— | H | 85–86 |
| 461 | 2,4,5-(CH₃)₃-C₆H₂ | CH₃(CH₂)₃— | H | 97–98 |
| 462 | 4-CH(CH₃)₂-C₆H₄ | CH₃(CH₂)₃— | H | 91 |
| 463 | 4-C(CH₃)₃-C₆H₄ | CH₃(CH₂)₃— | H | 74–76 |
| 464 | 2-OCH₃-C₆H₄ | CH₃(CH₂)₃— | H | 71–72 |
| 465 | 2-OC₂H₅-C₆H₄ | CH₃(CH₂)₃— | H | 74–75 |
| 466 | 2-OC₆H₅-C₆H₄ | CH₃(CH₂)₃— | H | 102–103 |
| 467 | 3-OCH₃-C₆H₄ | CH₃(CH₂)₃— | H | 57–58 |
| 468 | 3-OC₂H₅-C₆H₄ | CH₃(CH₂)₃— | H | 78 |
| 469 | 4-OCH₃-C₆H₄ | CH₃(CH₂)₃— | H | 89–91 |
| 470 | 4-OC₂H₅-C₆H₄ | CH₃(CH₂)₃— | H | 105 |
| 471 | 3-Cl-4-OCH₃-C₆H₃ | CH₃(CH₂)₃— | H | 114–115 |
| 472 | 4-OC₆H₅-C₆H₄ | CH₃(CH₂)₃— | H | 104–105 |
| 473 | 4-OCF₃-C₆H₄ | CH₃(CH₂)₃— | H | 142–143 |
| 474 | 3-Cl-4-SCH₃-C₆H₃ | CH₃(CH₂)₃— | H | 119–120 |
| 475 | 3-CH₃-4-OCH₃-C₆H₃ | CH₃(CH₂)₃— | H | 86–89 |
| 476 | 3-CH₃-4-OCH₃-C₆H₃ | CH₃(CH₂)₃— | H | 69–72 |
| 477 | 3-OCH₃-4-CH₃-C₆H₃ | CH₃(CH₂)₃— | H | 85–86 |
| 478 | 3-OC₂H₅-4-CH₃-C₆H₃ | CH₃(CH₂)₃— | H | 72–73 |
| 479 | 3,4-(OCH₃)₂-C₆H₃ | CH₃(CH₂)₃— | H | 84–86 |

| | | | | | | | | | |
|---|---|---|---|---|---|---|---|---|---|
| 480 | 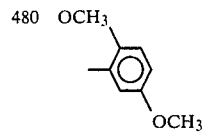 | CH₃(CH₂)₃— | H | 57–58 | 493 | 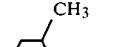 |  | H | 155–157 |
| 481 | 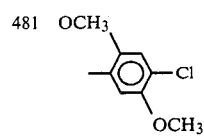 | CH₃(CH₂)₃— | H | 87–89 | 494 | 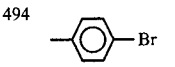 |  | H | 238–240 |
| | | | | | 495 |  |  | H | 193–195 |
| 482 | 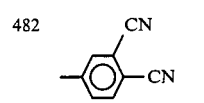 | CH₃(CH₂)₃— | H | 135–137 | 496 | 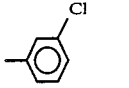 |  | H | 193–195 |
| 483 | 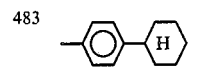 | CH₃(CH₂)₃— | H | 121 | 497 |  |  | H | 189–191 |
| 484 | 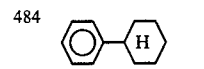 | CH₃(CH₂)₃— | H | 111–113 | | | | | |
| 485 | 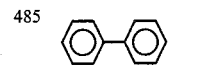 | CH₃(CH₂)₃— | H | 150 | 498 |  |  | H | 193–195 |
| 486 | 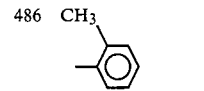 | CH₃₃(CH₂)₃— | H | 89 | 499 | 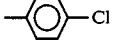 |  | H | 144–145 |
| 487 | 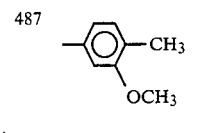 | CH₃(CH₂)₃— | H | 96–97 | 500 |  |  | H | 187–188 |
| 488 | 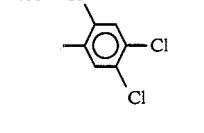 | CH₃(CH₂)₃— | H | 156–157 | 501 | 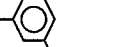 |  | H | 202–204 |
| 489 | 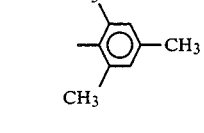 | CH₃(CH₂)₃— | H | 92–93 | 502 | 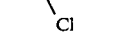 |  | H | 146–147 |
| | | | | | 503 | 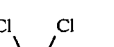 |  | H | 197–198 |
| 490 | 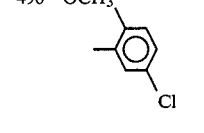 | CH₃(CH₂)₃— | H | 116–117 | 504 |  |  | H | 169–170 |
| 491 | 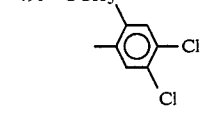 | CH₃(CH₂)₃— | H | 127–129 | 505 | 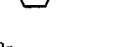 |  | H | 157–158 |
| 492 | 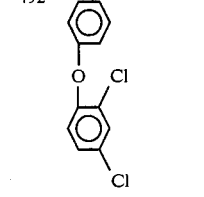 | CH₃(CH₂)₃— | H | 144–145 | 506 | 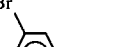 |  | H | 166–167 |
| | | | | | 507 |  |  | H | 192–193 |

-continued

| No. | Ar | R | R' | m.p. (°C) |
|---|---|---|---|---|
| 508 | 3-Cl, 4-CF₃-phenyl | phenyl | H | 136–137 |
| 509 | 3-Cl, 4-CH₃-phenyl | phenyl | H | 193–194 |
| 510 | 3-CH₃, 4-Br-phenyl | phenyl | H | 209–210 |
| 511 | 3-CH₃, 4-Cl-phenyl | phenyl | H | 168–169 |
| 512 | 2-CH₃, 3-Cl-phenyl | phenyl | H | 163–164 |
| 513 | 2-CF₃, 4-Cl-phenyl | phenyl | H | 128–129 |
| 514 | 2-C₂H₅-phenyl | phenyl | H | 124–125 |
| 515 | 4-C₂H₅-phenyl | phenyl | H | 174–175 |
| 516 | 2-CH₃, 4-Cl-phenyl | phenyl | H | 204–205 |
| 517 | 2,5-(CH₃)₂-phenyl | phenyl | H | 175–176 |
| 518 | 2-(CH₃)₂CH-phenyl | phenyl | H | 109–110 |
| 519 | 4-CH(CH₃)₂-phenyl | phenyl | H | 191–193 |
| 520 | 4-(CH₂)₃CH₃-phenyl | phenyl | H | 175–176 |
| 521 | 2,4-Cl₂-phenyl | C₂H₅ | H | 145 |
| 522 | 2,4,6-(CH₃)₃-phenyl | H | H | 149–150 |
| 523 | phenyl | CH₃(CH₂)₃ | H | 104–105 |
| 524 | phenyl | CH₃(CH₂)₄— | H | 94 |
| 525 | 2-Br-phenyl | CH₃(CH₂)₄— | H | 76 |
| 526 | 4-Br-phenyl | CH₃(CH₂)₄— | H | 154 |
| 527 | 2-Cl, 4-Br-phenyl | CH₃(CH₂)₄— | H | 122 |
| 528 | 2-Cl-phenyl | CH₃(CH₂)₄— | H | 92 |
| 529 | 4-Cl-phenyl | CH₃(CH₂)₄— | H | 146 |
| 530 | 2,3-Cl₂-phenyl | CH₃(CH₂)₄— | H | 106 |
| 531 | 2,5-Cl₂-phenyl | CH₃(CH₂)₄— | H | 108 |
| 532 | 2,4-Cl₂-phenyl | CH₃(CH₂)₄— | H | 108 |
| 533 | 2-F-phenyl | CH₃(CH₂)₄— | H | 104 |
| 534 | 4-F-phenyl | CH₃(CH₂)₄— | H | 126 |
| 535 | 3-CH₃-phenyl | CH₃(CH₂)₄— | H | 70 |
| 536 | 3-CF₃-phenyl | CH₃(CH₂)₄— | H | 79 |
| 537 | 2-Cl, 4-CH₃-phenyl | CH₃(CH₂)₄— | H | 96 |
| 538 | 2-CH₃, 4-Cl-phenyl | CH₃(CH₂)₄— | H | 96 |

| | | | | |
|---|---|---|---|---|
| 539 | 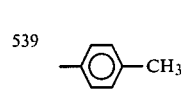 | CH₃(CH₂)₄— | H | 114 |
| 540 | 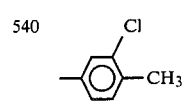 | CH₃(CH₂)₄— | H | 95 |
| 541 | 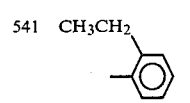 | CH₃(CH₂)₄— | H | 63 |
| 542 | 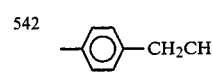 | CH₃(CH₂)₄— | H | 102 |
| 543 | 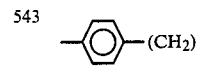 | CH₃(CH₂)₄— | H | 89 |
| 544 | 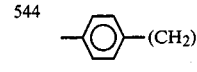 | CH₃(CH₂)₄— | H | 89 |
| 545 | 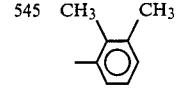 | CH₃(CH₂)₄— | H | 64 |
| 546 | 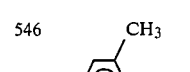 | CH₃(CH₂)₄— | H | 74 |
| 547 | 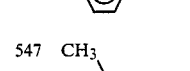 | CH₃(CH₂)₄— | H | 96 |
| 548 | 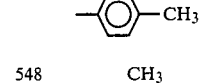 | CH₃(CH₂)₄— | H | 83 |
| 549 | 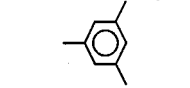 | CH₃(CH₂)₄— | H | 88 |
| 550 | 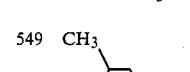 | CH₃(CH₂)₄— | H | 60 |
| 551 |  | CH₃(CH₂)₄— | H | 102 |
| 552 | 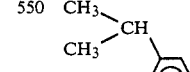 | CH₃(CH₂)₄— | H | 111 |
| 553 |  | CH₃(CH₂)₄— | H | 76 |
| 554 | 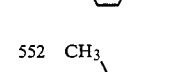 | CH₃(CH₂)₄— | H | 82 |
| 555 | 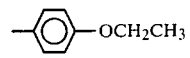 | CH₃(CH₂)₄— | H | 104 |
| 556 |  | CH₃(CH₂)₄— | H | 132 |
| 557 |  | CH₃(CH₂)₄— | H | 91 |
| 558 | 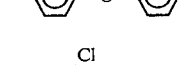 | CH₃(CH₂)₄— | H | 105 |
| 559 | 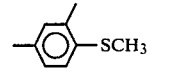 | CH₃(CH₂)₄— | H | 60 |
| 560 | 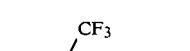 | CH₃(CH₂)₄— | H | 90 |
| 561 | 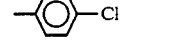 | CH₃(CH₂)₅— | H | 138 |
| 562 | 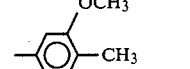 | CH₃(CH₂)₅— | H | 70 |
| 563 |  | CH₃(CH₂)₅— | H | 88 |
| 564 | 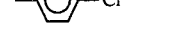 | CH₃(CH₂)₅— | H | 90 |
| 565 |  | CH₃(CH₂)₅— | H | 90 |
| 566 |  | CH₃(CH₂)₅— | H | 148 |
| 567 |  | CH₃(CH₂)₅— | H | 114 |
| 568 |  | CH₃(CH₂)₅— | H | 84 |
| 569 |  | CH₃(CH₂)₅— | H | 100 |
| 570 | 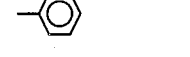 | CH₃(CH₂)₅— | H | 109 |
| 571 | 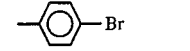 | CH₃(CH₂)₅— | H | 100 |

-continued

| # | Ar | R1 | R2 | mp |
|---|---|---|---|---|
| 572 | 4-F-C6H4 | CH3(CH2)5— | H | 120 |
| 573 | 2-Cl-5-CF3-C6H3 | CH3(CH2)5— | H | 60 |
| 574 | 3,4-Br2-C6H3 | CH3(CH2)5— | H | 116 |
| 575 | 4-Cl-3-CH3-C6H3 | CH3(CH2)5— | H | 74 |
| 576 | 4-Cl-3-CH3-C6H3 | CH3(CH2)5— | H | 94 |
| 577 | 4-Cl-3-CH3-C6H3 | CH3(CH2)5— | H | 89 |
| 578 | 4-CH3-C6H4 | CH3(CH2)5— | H | 106 |
| 579 | 4-CH2CH3-C6H4 | CH3(CH2)5— | H | 99 |
| 580 | 2-CH3CH2-C6H4 | CH3(CH2)5— | H | 61 |
| 581 | 2-CH3-5-Cl-C6H3 | CH3(CH2)5— | H | 90 |
| 582 | 2-Cl-3-CH3-C6H3 | CH3(CH2)5— | H | 62 |
| 583 | 3,5-(CH3)2-C6H3 | CH3(CH2)5— | H | 72 |
| 584 | 3-CF3-C6H4 | CH3(CH2)5— | H | 79 |
| 585 | 4-CH(CH3)2-C6H4 | CH3(CH2)5— | H | 90 |
| 586 | 2-CH3-C6H4-cyclohexyl | CH3(CH2)5— | H | 116 |
| 587 | 1-naphthyl | CH3(CH2)5— | H | 99 |
| 588 | 4-C6H5-C6H4 | CH3(CH2)5— | H | 142 |
| 589 | 4-(CH2)3CH3-C6H4 | CH3(CH2)5— | H | 91 |
| 590 | 2,3-(CH3)2-C6H3 | CH3(CH2)5— | H | 67 |
| 591 | 2,6-(CH3)2-C6H3 | CH3(CH2)5— | H | 70 |
| 592 | 2,4-(CH3)2-C6H3 | CH3(CH2)5— | H | 99 |
| 593 | 3,5-(CH3)2-C6H3 | CH3(CH2)5— | H | 71 |
| 594 | 2,4-(CH3)2-C6H3 | CH3(CH2)5— | H | 96 |
| 595 | 2-CH(CH3)2-C6H4 | CH3(CH2)5— | H | 42 |
| 596 | 4-OCH3-C6H4 | CH3(CH2)5— | H | 85 |
| 597 | 4-OCH2CH3-C6H4 | CH3(CH2)5— | H | 120 |
| 598 | 4-SCF3-C6H4 | CH3(CH2)5— | H | 127 |
| 599 | 2-OCH3-4-CH3-C6H3 | CH3(CH2)5— | H | 87 |
| 600 | 2,3-(CH3)2-C6H3 | C6H5 | H | 131 |
| 601 | 2-OCH3-4-Cl-C6H3 | C6H5 | H | 179 |
| 602 | 2-OCH3-4-Cl-5-OCH3-C6H2 | C6H5 | H | 132 |

-continued

| No. | R | R' | R'' | mp |
|---|---|---|---|---|
| 603 | 2-Cl-4-Me-C6H3-SCH3 | Ph | H | 197 |
| 604 | 2,4-(CH3O)2-C6H3 | Ph | H | 160 |
| 605 | 2-CH3O-4-CH3-C6H3 | Ph | H | 126 |
| 606 | 2-CH3-4-CH3O-C6H3 | Ph | H | 130 |
| 607 | 2,4-(CH3)2-C6H3 | Ph | H | 135 |
| 608 | 3,5-(CF3)2-C6H3 | Ph | H | 180 |
| 609 | 2-CH3-6-PhO-C6H3 | Ph | H | 134 |
| 610 | 3-CH3-C6H4-cyclohexyl | Ph | H | 204 |
| 611 | 4-cyclohexenyl-C6H4 | Ph | H | 152 |
| 612 | 2-CH3O-C6H4 | Ph | H | 155 |
| 613 | 2-CH3CH2O-C6H4 | Ph | H | 124 |
| 614 | 2-Cl-4-OCH3-C6H3 | Ph | H | 176 |
| 615 | 2-OCH3-4-CH3-C6H3 | Ph | H | 171 |
| 616 | 2-CH3O-4-OCH3-C6H3 | Ph | H | 168 |
| 617 | —CH2—Ph | CH3 | H | 65 |
| 618 | 2-CH3-4-Cl-C6H3 | CH3 | CH3 | 120 |
| 619 | cyclohexyl | CH3 | H | 83 |
| 620 | 2-Cl-3-CH3-C6H3 | cyclohexyl | H | 139 |
| 621 | 2,3-Cl2-C6H3 | cyclohexyl | H | 161 |
| 622 | 2-Cl-C6H4 | cyclohexyl | H | 124 |
| 623 | 4-OCF3-C6H4 | cyclohexyl | H | 178 |
| 624 | 2-CH3-3-Cl-C6H3 | cyclohexyl | H | 134 |
| 625 | 4-(CH2)2CH3-C6H4 | Ph | H | 180–181 |
| 626 | 4-OC2H5-C6H4 | Ph | H | 162 |
| 627 | 4-PhO-C6H4 | Ph | H | 198–199 |
| 628 | 4-C(CH3)3-C6H4 | Ph | H | 208 |
| 629 | 4-cyclohexyl-C6H4 | Ph | H | 168–170 |
| 630 | naphthyl | Ph | H | 129–130 |
| 631 | 2-PhO-C6H4 | Ph | H | 160 |
| 632 | 4-OCF3-C6H4 | Ph | H | 218–220 |
| 633 | 2,3-Br2-C6H3 | Ph | H | 203 |

-continued

| No. | R | R' | mp |
|---|---|---|---|
| 634 | 4-Cl-C₆H₄- | C₆H₅- | H | 134 |
| 635 | 4-F-C₆H₄- | C₆H₅- | H | 158 |
| 636 | 3-F-C₆H₄- | C₆H₅- | H | 172 |
| 637 | 3-CF₃-4-Cl-C₆H₃- | C₆H₅- | H | 170 |
| 638 | 2,4-(CH₃)₂-C₆H₃- | C₆H₅- | H | 138 |
| 639 | 2,3,4-(CH₃)₃-C₆H₂- | C₆H₅- | H | 165 |
| 640 | 2,4,5-(CH₃)₃-C₆H₂- | C₆H₅- | H | 165 |
| 641 | 4-(C₈H₁₇)-C₆H₄- | C₆H₅- | H | 158 |
| 642 | 4-(C₁₀H₂₁)-C₆H₄- | C₆H₅- | H | 152 |

USE EXAMPLES

The compounds shown below are used as comparison substances in the use examples which follow:

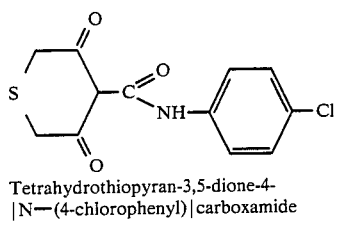

(A)

Tetrahydrothiopyran-3,5-dione-4-
|N—(4-chlorophenyl)|carboxamide

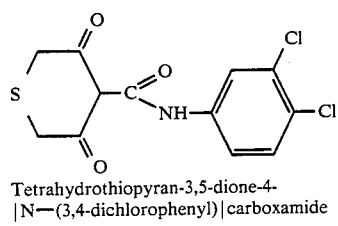

(B)

Tetrahydrothiopyran-3,5-dione-4-
|N—(3,4-dichlorophenyl)|carboxamide (both known from Japanese Pat. No. 77 46,078 of Apr. 12, 1977).

EXAMPLE A

Pyricularia test (rice)/protective

Solvent: 12.5 parts by weight of acetone.
Emulsifier: 0.3 parts by weight of alkylaryl polyglycol ether.

To produce a suitable preparation of active compound, 1 part by weight of active compound is mixed with the stated amount of solvent, and the concentrate is diluted with water and the stated amount of emulsifier, to the desired concentration.

To test for protective activity, young rice plants are sprayed with the preparation of active compound until dripping wet. After the spray coating has dried on, the plants are inoculated with an aqueous spore suspension of *Pyricularia oryzae*. The plants are then placed in a greenhouse at 100% relative atmospheric humidity and 25° C.

Evaluation of the disease infestation is carried out 4 days after the inoculation.

In this test, a clearly superior activity compared with the prior art is shown, for example, by the compounds according to preparation examples: 3, 23, 26, 40, 70 and 71.

EXAMPLE B

*Cochliobolus sativus* test (barley)/protective

Solvent: 100 parts by weight of dimethylformamide.
Emulsifier: 0.25 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dew-moist. After the spray coating has dried on, the plants are sprayed with a conidia suspension of *Cochliobolus sativus*. The plants remain in an incubation cabinet for 48 hours at 20° C. and 100% relative atmospheric humidity.

The plants are placed in a greenhouse at a temperature of about 20° C. and a relative atmospheric humidity of about 80%.

Evaluation is carried out 7 days after the inoculation.

In this test, a clearly superior activity compared with the prior art is shown, for example, by the compounds according to preparation examples: 41 and 42.

EXAMPLE C

Phytophthora Test (tomato)/protective

Solvent: 4.7 parts by weight of acetone.
Emulsifier: 0.3 parts by weight of alkylaryl polyglycol ether.

To produce a suitable preparation of active compound, 1 part by weight of active compound is mixed with the stated amounts of solvent and emulsifier, and the concentrate is diluted with water to the desired concentration.

To test for protective activity, young plants are sprayed with the preparation of active compound until dripping wet. After the spray coating has dried on, the plants are inoculated with an aqueous spore suspension of *Phytophthora infestans*.

The plants are placed in an incubation cabinet at 100% relative atmospheric humidity and at about 20° C.

Evaluation is carried out 3 days after the inoculation.

In this test, a clearly superior activity compared with the prior art is shown, for example, by the compounds according to preparation examples: 2 and 17.

EXAMPLE D

Plasmopara test (vines)/protective

Solvent: 4.7 parts by weight of acetone.
Emulsifier: 0.3 parts by weight of alkylaryl polyglycol ether.

To produce a suitable preparation of active compound, 1 part by weight of active compound is mixed with the stated amount of solvent and emulsifier, and the concentrate is diluted with water to the desired concentration.

To test for protective activity, young plants are sprayed with the preparation of active compound until dripping wet. After the spray coating has dired on, the plants are inoculated with an aqueous spore suspension of *Plasmopara viticola and then remain in a humidity chamber at 20° to 22° C. and 100% relative atmospheric humidity for 1 day. The plants are then placed in a greenhouse at 22° C. and about 80% atmospheric humidity for 5 days. The plants are then moistened and placed in a humidity chamber for 1 day.

Evaluation is carried out 7 days after the inoculation.

In this test, a clearly superior activity compared with the prior art is shown, for example, by the compounds according to preparation examples: 1 and 23.

It will be understood that the specification and examples are illustrative but not limitative of the present invention and that other embodiments within the spirit and scope of the invention will suggest themselves to those skilled in the art.

We claim:

1. A thiolane-2,4-dione-3-carboxamide of the formula

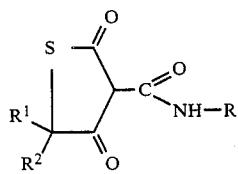

in which
R is alkyl, cycloalkyl, optionally substituted aralkyl or optionally substituted aryl,
$R^1$ is hydrogen, alkyl, cycloalkyl, cycloalkylalkyl, aralkyl or aryl and $R^2$ is hydrogen.

2. A thiolane-2,4-dione-3-carboxamide according to claim 1, in which
R is alkyl with 1 to 8 carbon atoms, cycloalkyl with 3 to 7 carbon atoms, aralkyl which has 1 or 2 carbon atoms in the alkyl part and 6 to 10 carbon atoms in the aryl part or aryl which has 6 to 10 carbon atoms, the aryl or aryl of aralkyl being independently substituted by halogen, cyano nitro, alkyl with 1 to 16 carbon atoms, alkoxy or alkylthio with in each case 1 to 4 carbon atoms, halogenoalkyl, halogenoalkoxy or halogenoalkylthio with in each case 1 or 2 carbon atoms and 1 to 5 identical or different halogen atoms, dioxyalkylene which has 1 or 2 carbon atoms in the alkylene radical, is linked in two positions and is optionally independently substituted by halogen and/or lower alkyl, phenyl or phenoxy, each of which is optionally independently substituted by halogen, lower alkyl and/or lower halogenoalkyl, and/or cycloalkyl with 5 to 7 carbon atoms, alkoxycarbonylalkyl or alkoxycarbonylalkenyl with in each case 1 or 2 carbon atoms in the alkoxy part and in each case 1 or 2 carbon atoms in the alkyl or alkenyl part,
$R^1$ is hydrogen, alkyl with 1 to 6 carbon atoms, cycloalkyl with 3 to 7 carbon atoms, cycloalkylalkyl with 3 to 7 carbon atoms in the cycloalkyl part and 1 or 2 carbon atoms in the alkyl part, phenylalkyl with 1 or 2 carbon atoms in the alkyl part or phenyl and $R^2$ is hydrogen.

3. A thiolane-2,4-dione-3-carboxamide according to claim 1, in which
R is alkyl with 1 to 6 carbon atoms, cyclopentyl, cyclohexyl, or phenyl, benzyl or naphthyl, each of which is optionally mono-, di- or tri-substituted by fluorine, chlorine, bromine nitro, cyano, alkyl with 1 to 14 carbon atoms, methoxy, ethoxy, methylthio, trifluoromethyl, trifluoromethoxy, trifluoromethylthio, dioxymethylene, dioxyethylene or dioxytrifluorochloroethylene, each of which is linked in two positions, phenyl and phenoxy, each of which is optionally mono-, di- or tri-substituted by methyl, chlorine and trifluoromethyl, and cyclopentyl, cyclohexyl, 2-methoxycarbonylvinyl and 2-ethoxycarbonylvinyl,
$R^1$ is hydrogen, methyl, ethyl, n- or i-propyl, n-, i-, s- or t-butyl, cyclohexyl, cyclohexylmethyl, benzyl or phenyl and $R^2$ is hydrogen.

4. A fungicidal composition comprising a fungicidally effective amount of a compound according to claim 1 in admixture with a diluent.

5. A method of combating fungi which comprises administering to such fungi or to a fungus habitat a fungicidally effective amount of a compound according to claim 1.

* * * * *

UNITED STATES PATENT AND TRADEMARK OFFICE
CERTIFICATE OF CORRECTION

PATENT NO. : 4,689,343

DATED : August 25, 1987

INVENTOR(S) : Herbert Gayer, et al.

It is certified that error appears in the above-identified patent and that said Letters Patent is hereby corrected as shown below:

| | |
|---|---|
| Title Page, Under "[22]" | Insert --[30] <u>Foreign Application Priority Data</u><br>3344523 Fed. Rep. of Germany December 9, 1983<br>3427847 Fed. Rep. of Germany July 27, 1984-- |
| Col. 3, line 3 | Delete "2" and substitute --4-- |
| Col. 3, lines 25 and 26 | Delete "to" and substitute --or-- |
| Col. 5, line 63 | End of formula delete "Hal" and substitute --Hal'-- |
| Col. 7, line 7 | Correct --Plasmodiophoromycetes-- |
| Col. 8, line 7 | Correct spelling of --natural-- |
| Col. 8, line 33 | Correct spelling of --phthalocyanine-- |
| Col. 9, line 23 | Delete "130°" and substitute --132°-- |
| Col. 35, Example 364 | Last column delete "180" and substutute --130-- |
| Col. 50, Example 597 | End of first formula delete "$OCH_2CH_2$" and substitute --$OCH_3CH_3$-- |

UNITED STATES PATENT AND TRADEMARK OFFICE
CERTIFICATE OF CORRECTION

PATENT NO. : 4,689,343

DATED : August 25, 1987

INVENTOR(S) : Herbert Gayer, et al.

Page 2 of 2

It is certified that error appears in the above-identified patent and that said Letters Patent is hereby corrected as shown below:

Col. 50, Example 598      End of first formula delete "$SCF_3$" and substitute --$OCF_3$--

Col. 55, line 21      Delete "dired" and substitute --dried--

Signed and Sealed this

Seventeenth Day of May, 1988

Attest:

DONALD J. QUIGG

Attesting Officer

Commissioner of Patents and Trademarks